United States Patent
Harding et al.

(10) Patent No.: US 8,636,148 B2
(45) Date of Patent: Jan. 28, 2014

(54) SORTING MINED MATERIAL

(75) Inventors: Damien Harding, Clifton Hill (AU); Grant Wellwood, Bundoora (AU)

(73) Assignee: Technological Resources Pty. Limited, Melbourne, Victoria (AU)

( * ) Notice: Subject to any disclaimer, the term of this patent is extended or adjusted under 35 U.S.C. 154(b) by 420 days.

(21) Appl. No.: 13/002,032

(22) PCT Filed: Sep. 11, 2009

(86) PCT No.: PCT/AU2009/001200
§ 371 (c)(1),
(2), (4) Date: Apr. 8, 2011

(87) PCT Pub. No.: WO2010/028447
PCT Pub. Date: Mar. 18, 2010

(65) Prior Publication Data
US 2011/0174904 A1      Jul. 21, 2011

(30) Foreign Application Priority Data
Sep. 11, 2008   (AU) ................................. 2008904740

(51) Int. Cl.
*B07C 5/34*       (2006.01)
(52) U.S. Cl.
USPC ............................. 209/11; 209/576; 209/577
(58) Field of Classification Search
USPC ................. 209/3, 11, 552, 576, 577; 250/253
See application file for complete search history.

(56) References Cited

U.S. PATENT DOCUMENTS

| | | | |
|---|---|---|---|
| 3,880,586 A * | 4/1975 | Murayama et al. ........... 422/108 |
| 5,209,355 A | 5/1993 | Mindermann | |
| 5,691,542 A * | 11/1997 | Bates et al. ................. 250/495.1 |
| 6,845,869 B1 * | 1/2005 | Graf von Deym et al. ... 209/522 |
| 7,541,557 B2 * | 6/2009 | Voloshyn et al. ............. 209/576 |
| 7,727,301 B2 * | 6/2010 | Shaw ............................ 75/10.13 |
| 8,083,066 B2 * | 12/2011 | Bourely ............................ 209/3 |
| 8,100,581 B2 * | 1/2012 | Djordjevic .................... 374/122 |
| 8,177,069 B2 * | 5/2012 | Valerio ........................... 209/11 |

(Continued)

FOREIGN PATENT DOCUMENTS

| GB | 2 076 146 A | 11/1981 |
|---|---|---|
| WO | WO 03/102250 A1 | 12/2003 |

(Continued)

OTHER PUBLICATIONS

International Search Report from the Australian Patent Office for International Application No. PCT/AU2009/001200, mailed Nov. 13, 2009.

*Primary Examiner* — Joseph C Rodriguez
(74) *Attorney, Agent, or Firm* — Banner & Witcoff, Ltd.

(57) ABSTRACT

A method of sorting mined material to separate the mined material is disclosed. The method comprises exposing particles of the mined material to microwave energy and heating the particles depending on the susceptibility of the material in the particles. The method also comprises thermally analyzing the particles using the temperatures of the particles as a basis for the analysis to indicate composition differences between particles. The thermal analysis step includes thermally assessing particles against a background surface. The thermal analysis step also includes heating the background surface to a temperature that is different to the temperature of the particles to provide a thermal contrast between the particles and the background surface. The method also comprises sorting the particles on the basis of the results of the thermal analysis.

15 Claims, 1 Drawing Sheet

(56) References Cited

U.S. PATENT DOCUMENTS

| | | | |
|---|---|---|---|
| 8,240,480 B2* | 8/2012 | Shaw et al. | 209/11 |
| 8,446,156 B2* | 5/2013 | Morrison | 324/637 |
| 2010/0206778 A1* | 8/2010 | Shaw et al. | 209/3 |
| 2011/0180638 A1* | 7/2011 | Harding et al. | 241/24.1 |
| 2011/0186660 A1* | 8/2011 | Harding et al. | 241/24.1 |

FOREIGN PATENT DOCUMENTS

| | | | | |
|---|---|---|---|---|
| WO | WO 2006/034553 A1 | 4/2006 | | |
| WO | WO 2007/051225 A1 | 5/2007 | | |
| WO | WO 2008046136 A1 * | 4/2008 | | B07C 5/342 |

\* cited by examiner

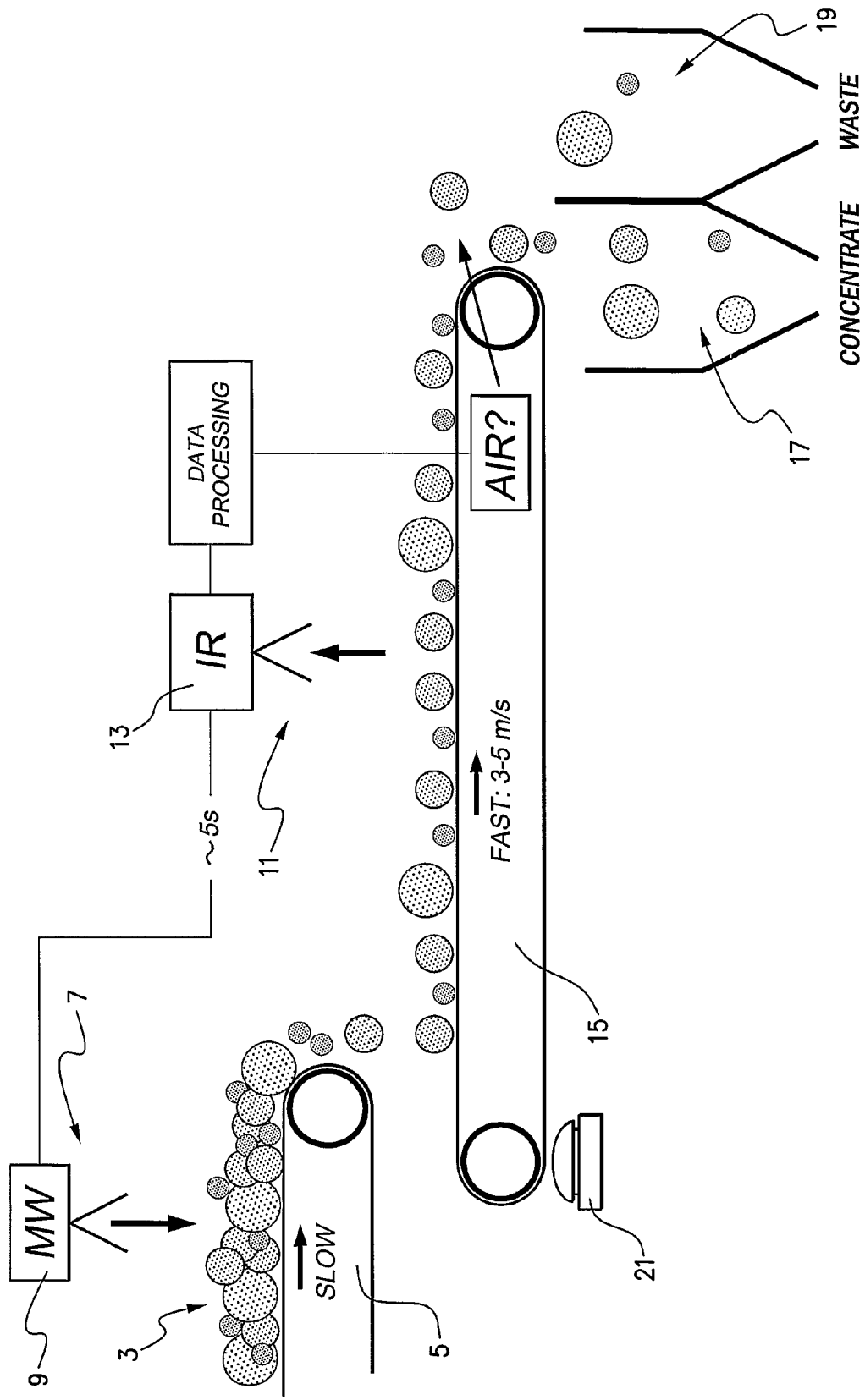

SORTING MINED MATERIAL

CROSS REFERENCE TO RELATED APPLICATIONS

This application is a national phase application based on PCT/AU2009/001200, filed Sep. 11, 2009, which claims the priority of Australian Patent Application No. 2008904740, filed Sep. 11, 2008, the content of both of which is incorporated herein by reference.

The present invention relates to a method and an apparatus for sorting mined material.

The present invention relates particularly, although by no means exclusively, to a method and an apparatus for sorting mined material for subsequent processing to recover valuable material, such as valuable metals, from the mined material.

The present invention also relates to a method and an apparatus for recovering valuable material, such as valuable metals, from mined material that has been sorted.

The mined material may be any mined material that contains valuable material, such as valuable metals, such as valuable metals in the form of minerals that comprise metal oxides or sulphides.

The term "mined" material is understood herein to include (a) run-of-mine material and (b) run-of-mine material that has been subjected to primary crushing or similar size reduction after the material has been mined and prior to being sorted.

A particular area of interest to the applicant is mined material in the form of mined ores that include minerals such as chalcopyrite that contain valuable metals, such as copper, in sulphide forms.

The present invention is particularly, although not exclusively, applicable to sorting low grade mined material.

The term "low" grade is understood herein to mean that the economic value of the valuable material, such as a metal, in the mined material is only marginally greater than the costs to mine and recover and transport the valuable material to a customer.

In any given situation, the concentrations that are regarded as "low" grade will depend on the economic value of the valuable material and the mining and other costs to recover the valuable material at a particular point in time. The concentration of the valuable material may be relatively high and still be regarded as "low" grade. This is the case with iron ores.

In the case of valuable material in the form of copper sulphide minerals, currently "low" grade ores are run-of-mine ores containing less than 1.0% by weight, typically less than 0.6 wt. %, copper in the ores. Sorting ores having such low concentrations of copper from barren particles is a challenging task from a technical viewpoint, particularly in situations where there is a need to sort very large amounts of ore, typically at least 10,000 tonnes per hour, and where the barren particles represent a smaller proportion of the ore than the ore that contains economically recoverable copper.

The term "barren" particles, when used in the context of copper-containing ores, are understood herein to mean particles with no copper or very small amounts of copper that can not be recovered economically from the particles.

The term "barren" particles when used in a more general sense in the context of valuable materials is understood herein to mean particles with no valuable material or amounts of valuable material that can not be recovered economically from the particles.

The present invention is based on a realisation that exposing mined material to microwave energy and heating particles containing copper minerals to higher temperatures than barren particles (as a consequence of the copper minerals) and subsequently thermally analysing the particles using the mass average temperatures of the particles that were exposed to microwave energy as a basis for the analysis is an effective method for sorting copper-containing particles from barren particles. In this context, the copper-containing particles can be described as being particles that are more susceptible to microwave energy and the barren particles can be described as being particles that are less susceptible to microwave energy and will not be heated to the same extent as copper-containing particles when exposed to microwave energy.

The present invention is also based on a realisation that selectively heating a background surface that is in a line of sight of a thermal analysis apparatus to a temperature that is different to the temperatures of the particles can improve the thermal analysis of particles in the line of sight between the apparatus and the background surface by making it possible to thermally differentiate more clearly between (a) the background surface and (b) the particles that are not heated at all or are heated only slightly by the microwave energy and the particles that are heated by the microwave energy.

In particular, the present invention is based on the finding of the applicant in relation to copper-containing ores that:

(a) as a consequence of the high susceptibility of copper minerals to microwave energy, even small concentrations of copper minerals in particles of mined material can cause detectable or measureable, albeit small, increases in temperature of the particles compared to the increases in temperature in other mined material which comprises barren particles and is less susceptible to microwave energy, and (b) having a background surface that is in a line of sight of a thermal analysis apparatus and is at or close to the same temperature as particles makes it very difficult to differentiate thermally between the background surface and the particles and this makes it very difficult to thermally "see" and then separate barren particles and particles containing copper minerals.

By selectively heating the background surface that is in the line of sight of the thermal detection apparatus makes it possible to contrast thermally between the background surface and particles, and this improves sorting, particularly from the viewpoint that particles can now be more easily seen thermally and then sorted.

According to the present invention there is provided a method of sorting mined material, such as mined ore, to separate the mined material into at least two categories, with at least one category containing particles of mined material that are more susceptible to microwave energy, and with at least one other category containing particles of mined material that are less susceptible to microwave energy, the method comprising the steps of:

(a) exposing particles of the mined material to microwave energy and heating the particles depending on the susceptibility of the material in the particles;

(b) thermally analysing the particles using the temperatures of the particles as a basis for the analysis to indicate composition differences between particles, the thermal analysis step including thermally assessing particles against a background surface, the thermal analysis step also including heating the background surface to a temperature that is different to the temperature of the particles to provide a thermal contrast between the particles and the background surface; and (c) sorting the particles on the basis of the results of the thermal analysis.

The basis of thermal analysis in step (b) may be that the mined material contains particles that have higher levels of valuable material, such as copper, that will respond differently thermally than more barren particles, i.e. particles with no or uneconomically recoverable concentrations of the valuable material, when exposed to microwave energy to an extent that the different thermal response can be used as a basis to sort particles.

The basis of the thermal analysis in step (b) may be that particles of the mined material that are more susceptible to microwave energy are less valuable material than the remainder of the mined material which is less susceptible to microwave energy to an extent that the different thermal response can be used as a basis to sort particles. An example of such a situation is coal that contains unwanted metal sulphides. The metal sulphides are more susceptible to microwave energy than coal.

The thermal analysis in step (b) may be carried out, for example, using known thermal analysis systems based on infrared detectors that can be positioned to view an analysis region, such as a region through which particles of mined material pass. These thermal analysis systems are commonly used in areas such as monitoring body temperature, examining electrical connections such as in sub-stations, and monitoring tanks and pipes and now have sufficient accuracy to detect small (i.e. <2° C.) temperature differences.

By way of example, in a situation in which the valuable material is copper and the copper is contained for example in a sulphide mineral in particles in ores, typically the copper-containing particles will be heated and the barren particles will not be heated at all or to anywhere near the same extent. Hence, in this situation the sorting step (c) comprises separating hotter particles from colder particles. In this case the thermal analysis is concerned with detecting directly or indirectly temperature differences between particles. It is noted that there may be situations in which barren particles are heated to higher temperatures than copper-containing particles because the particles contain other susceptible material.

The thermal analysis will include viewing the particles thermally and, necessarily this will involve moving the particles past the background surface, with an infrared camera or other thermal detection apparatus positioned to view the particles, and with the background surface being in the line of sight of the thermal detection apparatus. Hence, the thermal images will include thermal images of the background surface.

The background surface may be a conveyor belt on which the particles are being transported.

Another, although not the only other option, is that the background surface be a surface positioned in a line of sight of an infrared or other thermal detection apparatus positioned on the opposite side of a free-fall zone for particles.

Thermal analysis step (b) may comprise heating the background surface by any suitable means to any suitable temperature. A suitable temperature can readily be determined in any given situation having regard to the composition of the mined material.

In any given situation, the selection of the wavelength or other characteristics of the microwave energy will be on the basis of facilitating a different thermal response of the particles so that the different temperatures of the particles, which are indicative of different compositions, can be used as a basis for sorting the particles.

The method may comprise allowing sufficient time for the heat generated in the particles by exposure to microwave energy to be transferred through the particles so that the temperature of each particle on the surface of the particle is a measure of the mass average temperature through the particle. This ensures that at least substantially all of the particles that have copper minerals within the particles can be detected because the heat generated by the microwave energy contact has sufficient time to heat the whole of each particle.

The amount of time required for heat transfer will depend on a range of factors including, by way of example, the composition of the particles, the size of the particles, and the temperatures involved, including the temperature differences required to distinguish between more susceptible and less susceptible particles, which may equate to particles of valuable and non-valuable materials.

For example, in the case of low grade copper-containing ores having particle sizes of the order of 15-30 mm, the amount of time required is typically at least 5 seconds, more typically at least 10 seconds, and the temperature difference required is typically at least 2° C., and more typically at least 5-10° C., and for larger particle sizes typically larger time periods and temperature differences are required.

The method may comprise processing separated particles from sorting step (c) to recover valuable material from the particles.

It is noted that there may be situations where all of the mined material that is sorted is "valuable". In the broadest sense, the method of the present invention is an effective option to separate mined material on the basis of the susceptibilities of the components of the mined material to microwave energy. The exposure to microwave energy heats the material in response to the susceptibilities of the components of the material. There may be situations in which a mined material has "valuable" material that is susceptible to microwave energy and other material that is not susceptible to microwave energy but is nevertheless "valuable" material. Coal containing unwanted metal sulphides mentioned above is one example. The metal sulphides may be unwanted in the context of the marketability of coal but may be valuable nevertheless when separated from coal.

The method may comprise reducing the size of separated particles from sorting step (c) that contain higher levels of valuable material to facilitate improved recovery of valuable material from the particles.

The further processing of the separated particles may be any suitable step or steps including, by way of example only, any one or more of heap leaching, pressure oxidation leaching, and smelting steps.

The method may comprise crushing or other suitable size reduction of the mined material prior to step (a).

One example of a suitable option for step (a) is to use high pressure grinding rolls.

The method may also comprise screening or otherwise separating fines from the mined material so that there are no fines in the mined material that is supplied to step (a). In the case of copper-containing ores, the term "fines" is understood to mean minus 13 mm size particles.

Typically, the manageable particle size distribution is one with particles having a major dimension in a range of 13-100 mm.

The particle size distribution may be selected as required. One relevant factor to the selection of particle size distribution may be the time required for the temperature of the surface of particles to be a measure of the mass average temperature of the particles. Another relevant factor may be the extent to which it is possible to "tune" the microwave energy characteristics (i.e. frequency, etc) to particular particle size distributions. The issue of particle size distributions, particularly the lower end of distributions, is particularly important when considering ore sorting of larger throughputs of ore.

The term "microwave energy" is understood herein to mean electromagnetic radiation that has frequencies in the range of 0.3-300 GHz.

Step (a) may comprise using pulsed or continuous microwave energy to heat the mined material.

Step (a) may comprise causing micro-cracking in particles of the mined material.

Whilst it is particularly desirable in some situations that step (a) cause micro-cracking of the particles of the mined material, preferably step (a) does not lead to significant breakdown of the particles at that time.

Step (a) may include any suitable step or steps for exposing mined ore to microwave energy.

One option is to allow mined ore to free-fall down a transfer chute past a microwave energy generator, such as described in International publication number WO 03/102250 in the name of the applicant.

Another, although not the only other, option is to pass the ore through a microwave cavity on a horizontally disposed conveyor belt or other suitable moving bed of material.

The moving bed may be a mixed moving bed, with a microwave generator positioned to expose ore to microwave energy such as described in International publication number WO 06/034553 in the name of the applicant.

The term "moving mixed bed" is understood to mean a bed that mixes ore particles as the particles move through a microwave exposure zone or zones and thereby changes positions of particles with respect to other particles and to the incident microwave energy as the particles move through the zone or zones.

Sorting step (c) may be any suitable step or steps for sorting the particles on the basis of the results of the thermal analysis.

For example, step (c) may comprise using a fluid, such as air or water, jets to deflect a downwardly flowing stream of the particles.

The mined material may be in the form of ores in which the valuable material is in a mineralised form such as a metal sulphide or oxide.

The applicant is interested particularly in copper-containing ores in which the copper is present as a sulphide mineral.

The applicant is also interested in molybdenum-containing ores in which the molybdenum is present as a sulphide mineral.

The applicant is also interested in nickel-containing ores in which the nickel is present as a sulphide mineral.

The applicant is also interested in uranium-containing ores.

The applicant is also interested in ores containing iron minerals where some of the iron minerals have disproportionately higher levels of unwanted impurities.

The applicant is also interested in diamond ores where the ore has a mix of diamond containing minerals and diamond barren minerals such as quartz.

According to the present invention there is also provided an apparatus for sorting mined material, such as mined ore, that comprises:

(a) a microwave treatment station for exposing particles of the mined material to microwave energy;

(b) a thermal analysis station for detecting thermal differences between particles from the microwave treatment station that indicate composition differences between particles that can be used as a basis for sorting particles, the thermal analysis station including a thermal detector positioned to view particles moving past a background surface, and the thermal analysis station including a system for heating the background surface to a predetermined temperature to provide a suitable thermal contrast with the particles; and (c) a sorter for sorting the particles on the basis of the thermal analysis.

The thermal analysis station may be arranged in relation to the microwave treatment station so that the particles have sufficient time for the heat generated in the particles by exposure to microwave energy in the microwave treatment station to be transferred through the particles so that the temperature of each particle on the surface of the particle is a measure of the mass average temperature through the particle.

The apparatus may comprise an assembly, such as a conveyor belt or belts, for transporting the particles of the mined material from the microwave treatment station to the thermal analysis station.

The thermal analysis station may comprise a conveyor belt for transporting the particles of the mined material through the station, with the thermal detector being positioned to view particles on the conveyor belt, whereby the conveyor belt forms the background surface, and the heating system for the background surface comprises a system for heating the conveyor belt.

The thermal analysis station may comprise the thermal detector positioned on one side of a free-fall zone for particles, and the background surface is a wall positioned on the opposite side of the zone.

According to the present invention there is also provided a method for recovering valuable material, such as a valuable metal, from mined material, such as mined ore, that comprises sorting mined material according to the method described above and thereafter processing the particles containing valuable material and recovering valuable material.

The present invention is described further by way of example with reference to the accompanying drawing which is a schematic diagram which illustrates one embodiment of a sorting method in accordance with the present invention.

The embodiment is described in the context of a method of recovering a valuable metal in the form of copper from low grade copper-containing ores in which the copper is present as a copper mineral, such as chalcopyrite. Typically, the ore contains 30-40 wt. % barren particles. The objective of the method in this embodiment is to separate the barren particles and the copper-containing particles. The copper-containing particles can then be processed as required to recover copper from the particles. Separating the copper-containing particles prior to the downstream recovery steps significantly increases the average grade of the material being processed in these steps.

It is noted that the present invention is not confined to these ores and to copper as the valuable material to be recovered.

With reference to the drawing, a feed material in the form of ore particles 3 that have been crushed by a primary crusher (not shown) to a particle size of 10-25 cm are supplied via a conveyor 5 (or other suitable transfer means) to a microwave energy treatment station 7 and are moved past a microwave energy generator 9 and exposed to microwave energy, either in the form of continuous or pulsed microwaves.

The microwave energy causes localised heating of particles depending on the composition of the particles. In particular, the particles are heated to different extents depending on whether or not the particles contain copper minerals, such as chalcopyrite, that are susceptible to microwave energy. As is indicated above, the applicant has found that particles having relatively small concentrations of copper, typically less than 0.5 wt. %, are heated to a detectable or measurable, albeit small, extent by microwave energy due to the high susceptibility of copper. This is a significant finding in relation to low grade ores because it means that relatively low concentrations of copper in particles can produce detectable or measurable temperature increases. However, as indicated above, the applicant has also found that there is a timing effect as to when the heat that is generated in particles will become detectable by thermal analysis. This timing effect is a function of whether the copper minerals are on the surface or within the particles and the size of the particles. In particular, the applicant has found that a time period of at least 5 seconds, typically at least 5-10 seconds, for the particle sizes mentioned above is necessary to allow heat transfer within each particle so that there is a substantially uniform, i.e. average mass temperature of the particle (including at the surface of the particle) and hence the thermal analysis provides accurate information on the particles. In other words, the surface temperatures of the particles are the mass average temperatures of the particles.

The basis of thermal analysis in this embodiment is that particles that contain higher levels of copper minerals will become hotter than barren particles.

The particles can be formed as a relatively deep bed on the conveyor belt 5. The bed depth and the speed of the belt and the power of the microwave generator are inter-related. The key requirement is to enable sufficient exposure of the particles to microwave energy to heat the copper minerals in the particles to an extent required to allow these particles to be distinguished thermally from barren particles. Whilst it is not always the case, typically the barren particles comprise material that is less susceptible than copper minerals and are not heated significantly, if at all, when exposed to microwave energy. A secondary requirement is to generate sufficient temperature variations within particles containing copper to cause micro-cracking of the particles, without breaking the particles down at that stage. The micro-cracking can be particularly beneficial in downstream processing of the particles. For example, the micro-cracking makes it possible for better access of leach liquor into particles in a downstream leach treatment to remove copper from particles. In addition, for example, the micro-cracking makes it possible for better particle break-down in any downstream size reduction step. An important point is that micro-cracking tends to occur where the temperature gradient within particles is the highest, at the interface between copper minerals and gangue material in particles. As a consequence, when the ore is subsequently milled (as is typically the case in downstream processing) copper minerals separate from the gangue material more readily in view of the micro-cracks at the interfaces, thereby producing discrete copper mineral and gangue particles. This preferred liberation is advantageous for downstream processing.

The particles that pass through the microwave treatment station 7 drop from the end of the conveyor belt 5 onto a lower conveyor belt 15 and are transported on this belt through an infra-red radiation detection station 11 at which the particles are viewed by an infra-red camera 13 (or other suitable thermal detection apparatus) and are analysed thermally. The conveyor belt 15 is operated at a faster speed than the conveyor belt 5 to allow the particles to spread out along the belt 15. This is helpful in terms of the downstream processing of the particles.

The spacing between the stations 7 and 11 is selected having regard to the belt speed to allow sufficient time, typically at least 5 seconds, for the particles to be heated uniformly within each particle.

Advantageously, the upstream processing conditions are selected so that the particles have sufficient retained heat for thermal analysis without additional heating of the particles being required. If additional heating is required, it can be provided by any suitable means.

In one mode of operation the thermal analysis is based on distinguishing between particles that are above and below a threshold temperature. The particles can then be categorised as "hotter" and "colder" particles. The temperature of a particle is related to the amount of copper minerals in the particle. Hence, particles that have a given particle size range and are heated under given conditions will have a temperature increase to a temperature above a threshold temperature "x" degrees if the particles contain at least "y" wt. % copper. The threshold temperature can be selected initially based on economic factors and adjusted as those factors change. Barren particles will generally not be heated on exposure to microwave energy to temperatures above the threshold temperature.

In this arrangement the conveyor belt 15 is a background surface. More particularly, the section of the conveyor belt 15 that is viewed by the infra-red camera 13 is a background surface and becomes a part of the thermal image of the camera. In order to provide thermal contrast between the background surface and the particles viewed by infra-red camera 13, the conveyor belt 15 is heated by a suitable heating assembly 21 to a temperature that is between the "hotter" and the "colder" particles. The thermal contrast provided by the heated conveyor belt 15 makes it possible to clearly identify the hotter and the colder particles. In particular, the heated conveyor belt 15 makes it possible to identify the colder particles against the conveyor belt.

Once identified by thermal analysis, the hotter particles are separated from the colder particles and the hotter particles are thereafter processed to recover copper from the particles. Depending on the circumstances, the colder particles may be processed in a different process route to the hotter particles to recover copper from the colder particles.

The particles are separated by being projected from the end of the conveyor belt 15 and being deflected selectively by compressed air jets (or other suitable fluid jets, such as water jets) as the particles move in a free-fall trajectory from the belt 15 and thereby being sorted into two streams 17, 19. In this connection, the thermal analysis identifies the position of each of the particles on the conveyor belt 15 and the air jets are activated a pre-set time after a particle is analysed as a particle to be deflected.

Depending on the particular situation, the gangue particles may be deflected by air jets or the particles that contain copper above a threshold concentration may be deflected by air jets.

The hotter particles become a concentrate feed stream 17 and are transferred for downstream processing, typically including milling, flotation to form a concentrate, and then further processing to recover copper from the particles.

The colder particles may become a by-product waste stream 19 and are disposed of in a suitable manner. This may not always be the case. The colder particles have lower concentrations of copper minerals and may be sufficiently valuable for recovery. In that event, the colder particles may be transferred to a suitable covery process, such as leaching.

Many modifications may be made to the embodiment of the present invention described above without departing from the spirit and scope of the present invention.

By way of example, whilst the embodiment includes heating the background surface to contrast thermally the background surface and the valuable particles and the barren particles, the present invention is not so limited and extends to heating the background surface to contrast thermally the background surface and one or other of the valuable particles and the barren particles.

By way of example, whilst the embodiment includes thermal analysis using an infra-red camera positioned above heated ore particles on a horizontally disposed conveyor belt 15, the present invention is not so limited and extends to other possible arrangements of cameras and to the use of other types of thermal imaging analysis. One such arrangement comprises allowing the heated particles to free-fall downwardly and arranging an infra-red camera to view a section of the downward flight path. Advantageously, this arrangement includes a background surface facing the camera. In use, the camera views downwardly moving particles and the background surface. The background surface is heated selectively to improve the thermal contrast between the surface and the particles.

By way of further example, whilst the embodiment includes the use of air jets to deflect particles selectively, the present invention is not so limited and extends to the use of other types of air deflection devices and to other options for deflecting particles.

By way of further example, whilst the embodiment includes the use of two conveyor belts 5, 15 to transport mined ore past the microwave treatment station 7 and the thermal analysis station 7, with the lower belt travelling at a higher speed than the upper belt to separate the particles on the belt to facilitate clearer thermal analysis of the particles, the present invention is not so limited and extends to any suitable alternative arrangements.

The invention claimed is:

1. A method of sorting mined material to separate mined material into at least two categories, the method comprising the steps of:
   (a) exposing particles of mined material to microwave energy and heating the particles depending on the susceptibilities and therefore the compositions of the materials in the particles;
   (b) thermally analysing the particles using the temperatures of the particles as a basis for the analysis to indicate composition differences between particles, with particles containing higher levels of valuable material than other particles falling into one category and particles containing no or uneconomically recoverable concentrations of valuable material than other particles falling into another category, with particles of one category responding differently thermally to particles of the other category to exposure to microwave energy, with the particles in one category being hotter than particles in the other category, the thermal analysis step including thermally assessing particles against a background surface, the thermal analysis step including heating the background surface to a temperature that is between the hotter particles in the one category and the colder particles in the other category to provide a thermal contrast between the particles in each category and the background surface; and
   (c) sorting particles on the basis of the results of the thermal analysis into the two categories.

2. The method defined in claim 1 wherein, in a situation in which the valuable material is copper and the copper is contained as a sulphide mineral in particles in ores, step (a) comprises exposing the mined ores to microwave energy and heating the copper-containing particles to a greater extent than barren particles.

3. The method defined in claim 1 wherein step (b) comprises moving the particles past the background surface, with an infrared camera or other thermal detection apparatus positioned to view the particles, and with the background surface being in the line of sight of the thermal detection apparatus.

4. The method defined in claim 1 comprises selecting the wavelength or other characteristics of the microwave energy on the basis of facilitating a different thermal response of the particles.

5. The method defined in claim 1 comprises allowing sufficient time for the heat generated in the particles by exposure to microwave energy to be transferred through the particles so that the temperature of each particle on the surface of the particle is a measure of the mass average temperature through the particle.

6. The method defined in claim 5 wherein, in the case of low grade copper-containing ores having particle sizes of the order of 15-30 mm, the amount of time required is at least 5 seconds and the temperature difference required is at least 2° C.

7. The method defined in claim 1 comprises processing separated particles from sorting step (c) to recover valuable material from the particles.

8. The method defined in claim 1 comprises reducing the size of separated particles from sorting step (c) that contain higher levels of valuable material to facilitate improved recovery of valuable material from the particles.

9. The method defined in claim 1 comprises crushing or other suitable size reduction of the mined material prior to step (a).

10. The method defined in claim 1 comprises screening or otherwise separating fines from the mined material so that there are no fines in the mined material that is supplied to step (a).

11. The method defined in claim 1 wherein the mined material is in the form of ores in which the valuable material is in a mineralised form.

12. A method for recovering valuable material from mined material comprising sorting mined material according to the method defined in claim 1 and thereafter processing the particles containing valuable material and recovering valuable material.

13. The method defined in claim 6 wherein, in the case of low grade copper-containing ores having particle sizes of the order of 15-30 mm, the amount of time required is at least 10 seconds.

14. The method defined in claim 6 wherein, in the case of low grade copper-containing ores having particle sizes of the order of 15-30 mm, the temperature difference is 5-10° C.

15. The method defined in claim 11 wherein the mined material is a metal sulphide or oxide.

* * * * *

UNITED STATES PATENT AND TRADEMARK OFFICE
CERTIFICATE OF CORRECTION

PATENT NO. : 8,636,148 B2  Page 1 of 1
APPLICATION NO. : 13/002032
DATED : January 28, 2014
INVENTOR(S) : Harding et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 448 days.

Signed and Sealed this
Twenty-second Day of September, 2015

Michelle K. Lee
*Director of the United States Patent and Trademark Office*